| United States Patent [19] | [11] | 4,424,364 |
|---|---|---|
| Goetz et al. | [45] | Jan. 3, 1984 |

[54] PREPARATION OF PYRAZOLES

[75] Inventors: Norbert Goetz, Worms; Dietrich Mangold, Neckargemuend; Josef Wahl, Schifferstadt, all of Fed. Rep. of Germany

[73] Assignee: BASF Aktiengesellschaft, Fed. Rep. of Germany

[21] Appl. No.: 283,650

[22] Filed: Jul. 15, 1981

[30] Foreign Application Priority Data

Aug. 1, 1980 [DE] Fed. Rep. of Germany ....... 3029160

[51] Int. Cl.$^3$ ............................................ C07D 231/12
[52] U.S. Cl. .................................... 548/373; 548/375; 548/378
[58] Field of Search ...................... 548/373, 375, 378

[56] References Cited

U.S. PATENT DOCUMENTS

| 3,896,143 | 7/1975 | Kathawala | 548/378 |
| 3,952,010 | 4/1976 | Garber et al. | 548/373 |
| 4,014,896 | 3/1977 | Garber et al. | 548/373 |
| 4,239,901 | 12/1980 | Rainer | 548/378 |

FOREIGN PATENT DOCUMENTS 1477020 6/1977 United Kingdom .

OTHER PUBLICATIONS

Neuere Methoden Der Praparativen Organischen Chemie, 2nd Edition, Part 1, (1944), Spriner Verlag, pp. 72-73.
Grandberg et al., Zhurnal Obshchei Kihimii 1958, vol. 28 (11), pp. 3071-3075.
Pershin et al., Doklady Akademii Nauk S.S.S.R. (U.S.S.R.) 1958, vol. 123 (1), pp. 200-203.
Wiley, Ed., Pyrazoles, Pyrazolines, Pyrazolidines, Indazoles and Condensed Rings (Interscience, New York, 1967), p. 215.

Primary Examiner—Richard Raymond
Attorney, Agent, or Firm—Keil & Witherspoon

[57] ABSTRACT

A process for the preparation of pyrazoles by reacting a pyrazoline with sulfur or selenium in a solvent.

3 Claims, No Drawings

PREPARATION OF PYRAZOLES

The present invention relates to a novel process for the preparation of pyrazoles.

Chemistry of Carbon Compounds, Volume IV a (Elsevier, N.Y., 1957), pages 246–249, describes numerous methods of synthesis of pyrazoles, for example by reacting a hydrazine with a 1,3-dicarbonyl compound, dehydrating a hydrazone of a β-keto-ester, cyclizing a hydrazone of an α-cyano-ketone, reacting an aldehydephenylhydrazone with a β-keto-ester in the presence of zinc chloride, or condensing an α-halohydrazone with a sodium keto compound or a diazo compound with an acetylene derivative. The more important methods of synthesis entail the reaction of a derivative of a 1,3-dicarbonyl compound with hydrazine or a hydrazine derivative in an acid aqueous solution, or with a salt of hydrazine or of a hydrazine derivative, to give a dilute aqueous solution of a pyrazole salt.

In all these methods of synthesis, and especially in the case of the synthesis of unsubstituted pyrazole or of pyrazoles which are substituted in the 1- or 4-position, it is necessary to resort to intermediates which are difficult to obtain and are expensive to prepare or present safety problems.

Problems of this type arise to a substantially lesser degree if pyrazole or pyrazole derivatives are prepared by dehydrogenation of pyrazoline or pyrazoline derivatives.

Pyrazoline itself, and pyrazoline derivatives, are readily obtainable from industrial starting materials, cf. G. Wirsing, J. prakt. Chemie (2) 50, 538.

Hitherto, the only methods disclosed for dehydrogenating unsubstituted pyrazoline, in particular, have been unsatisfactory especially from the point of view of preparative feasibility. The problems are described in detail by Grandberg and Kost (J. Gen. Chem. 28 (1958), 3102). These authors discovered that the reaction of elementary sulfur or selenium with pyrazolines constitutes a method of dehydrogenation which in the case of numerous alkylpyrazolines, and at reaction temperatures of from 150° to 250° C., gives 65–96% yields of alkylpyrazoles in a reaction which is strongly exothermic and is evidently difficult to control even on a small laboratory scale.

The method described is unsuitable for the preparation of larger amounts (the Examples having been carried out with 0.2 mole quantities), and is in no way capable of scale-up to industrial operation, since the yield of the process greatly decreases as the batch size increases.

We have found that pyrazolines, and in particular unsubstituted pyrazoline, can be converted to the corresponding pyrazoles even at temperatures starting from as low as 50° C., if sulfur or selenium in a solvent is employed for the dehydrogenation.

The pyrazoles obtained are very pure. The reaction can be represented by the following equation:

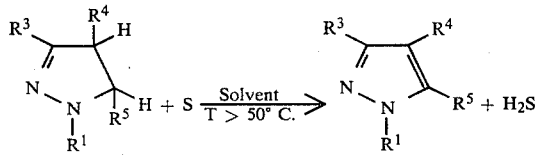

In the above formulae, the radicals $R^1$, $R^3$, $R^4$ and $R^5$ can be identical or different and each can be hydrogen or an aliphatic, araliphatic or aromatic radical. $R^3$ can also be halogen, $C\equiv N$ or $OR^6$, where $R^6$ is an aliphatic, araliphatic or aromatic radical. $R^1$ can also be $O-CO-R^2$, where $R^2$ is an aliphatic, araliphatic or aromatic radical. Preferably, the radicals $R^1$, $R^3$, $R^4$ and $R^5$ are hydrogen.

The amount of dehydrogenating agent employed is not critical; in general, a pyrazoline: sulfur molar ratio of from 1:1 to 1:3, preferably of 1:1, is used.

The amount of solvent or solvent mixture employed can also vary within wide limits and is preferably from 0.5 to 20 times the amount of pyrazoline employed.

In carrying out the reaction, the preferred procedure is to introduce the pyrazoline at a uniform rate into the sulfur or selenium solution or suspension, which has been heated to the reaction temperature, so that the hydrogen sulfide (or hydrogen selenide) evolved can readily be absorbed or worked up. Heating the reaction mixture is continued until the evolution of gas has ceased, and the mixture is then worked up in a conventional manner, for example by distillation or extraction.

The pyrazolines employed can be, for example, pyrazoline, 2-methylpyrazoline, 3-methylpyrazoline, 2,4-dimethylpyrazoline, 2-t-butylpyrazoline, 3-chloropyrazoline or halopyrazoline, 2-ethyl-3-methoxypyrazoline and 1-acetoxy-2,4-dimethylpyrazoline.

Examples of suitable solvents are aromatic hydrocarbons, eg. toluene, ethylbenzene, o-, m- and p-xylene, isopropylbenzene and methylnaphthalene; halohydrocarbons, especially chlorohydrocarbons, eg. tetrachloroethylene, 1,1,2,2- or 1,1,1,2-tetrachloroethane, amyl chloride, dichloropropane, methylene chloride, dichlorobutane, carbon tetrachloride, 1,1,1- or 1,1,2-trichloroethane, trichloroethylene, pentachloroethane, 1,2-dichloroethane, 1,1-dichloroethane, n-propyl chloride, 1,2-cis-dichloroethylene, n-butyl chloride, 2-, 3- and iso-butyl chloride, chlorobenzene, o-, p- and m-dichlorobenzene, o-, m- and p-chlorotoluene and 1,2,4-trichlorobenzene; ethers, eg. ethyl propyl ether, methyl tert.-butyl ether, n-butyl ethyl ether, di-n-butyl ether, diisobutyl ether, diisoamyl ether, diisopropyl ether, cyclohexyl methyl ether, diethyl ether, ethylene glycol dimethyl ether, tetrahydrofuran and dioxane; alkanols and cycloalkanols, eg. ethanol, methanol, n-butanol, isobutanol, tert.-butanol, glycol, n-propanol, isopropanol, amyl alcohol, cyclohexanol, 2-methyl-4-pentanol, ethylene glycol monoethyl ether, 2-ethylhexanol and methylglycol, alkanols of 1 to 4 carbon atoms being preferred; aliphatic and cycloaliphatic hydrocarbons, eg. heptane, pinane, nonane, gasoline fractions boiling within a range of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; and appropriate mixtures.

It is also possible to use nitrogen-containing polar solvents, eg. pyridine, alkylpyridines, technical alkylpyridine mixtures, alkylaminopyridines, quinoline, alkylquinolines, morpholine, alkylmorpholines, alkyl-substituted ureas, eg. tetramethylurea, N-methylpyrrolidone, amides, eg. dimethylformamide and dibutylformamide, ethylhexanoic acid dimethylamide, toluic acid diethylamide, N,N-dimethylimidazolidone, azoles, eg. pyrazole, and amines, eg. tributylamine or tripropylamine. Sulfur-containing solvents, such as sulfolane or dimethyl sulfoxide, can also be used.

Particularly preferred solvents are pyridine, technical alkylpyridine mixtures and mixtures of solvents, for example hydrocarbons, i.e. a mixture of pyridine and a hydrocarbon.

If pyrazole, or a mixture of pyrazole with, for example, toluene, is used as the solvent, the process can be carried out particularly simply.

Advantageously, the solvent is used in an amount of from 400 to 10,000 percent by weight, preferably from 100 to 500 percent by weight, based on pyrazoline.

The novel process can readily be carried out on an industrial scale and can be controlled safely.

The pyrazoles obtainable by the process of the invention are valuable starting materials for the preparation of crop protection agents, drugs and dyes.

EXAMPLE 1

200 ml of pyridine and 16 g of sulfur (0.5 mole) are introduced into a stirred apparatus. The mixture is heated to 110° C. and 35 g (0.5 mole) of 2-pyrazoline are added dropwise at a uniform rate, whilst stirring. A vigorous evolution of gas occurs. When this has subsided, the mixture is distilled under reduced pressure. 31 g (92%) of pyrazole, of excellent purity, are obtained at a boiling point of 90°–100° C./31 mm Hg.

Using a similar method, but with 200 ml of N-methylmorpholine, n-butanol or toluene as the solvent, the respective amounts of colorless pyrazole obtained are 29 g (85%), 21.4 g (63%) and 19.4 g (57%).

EXAMPLE 2

1,500 ml of toluene, 500 ml of pyridine and 160 g of sulfur are introduced into a stirred apparatus and 350 g of pyrazoline are then added dropwise to the mixture, at 105°–110° C., at a rate such that a vigorous but uniform evolution of gas occurs. Stirring is continued until the evolution of gas has subsided. The reaction mixture is distilled under reduced pressure. 300 g (88%) of almost colorless pyrazole, melting point 68° C., are obtained.

If the pyridine is replaced by 500 ml of pyrazole, an additional 283 g (83%) of pyrazole, of melting point 68° C., are obtained.

EXAMPLE 3

200 ml of a technical-grade pyridine base mixture (boiling point 80°–160° C.) and 16 g of sulfur are heated to 110° C. in a stirred apparatus. 42 g of 2-methylpyrazoline are added dropwise and stirring of the reaction mixture is continued until the evolution of gas has ceased. The mixture is then distilled under reduced pressure. 36.5 g (89%) of 2-methylpyrazole, boiling point 120° C./20 mm Hg, are obtained; according to gas-chromatographic analysis, the prouct is 95% pure.

EXAMPLE 4

180 ml of toluene, 20 g of 4-dimethylaminopyridine and 16 g of sulfur (0.5 mole) are introduced into a stirred apparatus. The mixture is heated to 110° C. and 35 g (0.5 mole) of 2-pyrazoline are added dropwise at a uniform rate, whilst stirring. A vigorous evolution of gas occurs. When this has subsided, the mixture is distilled under reduced pressure. 28 g (82%) of pyrazole are obtained at a boiling point of 90°–100° C./20 mm Hg.

We claim:

1. In a process for producing pyrazole by reacting pyrazoline with sulfur at a temperature above 50° C., the improvement which comprises:
   carrying out the reaction in a solvent of pyridine or a mixture of pyridine and a hydrocarbon.

2. The process of claim 1, wherein pyrazole is prepared by reacting pyrazoline with sulfur in a solvent of pyridine.

3. The process of claim 1, wherein the reaction is carried out at from 80° to 120° C.

* * * * *